(12) United States Patent
Barker et al.

(10) Patent No.: US 11,598,899 B2
(45) Date of Patent: Mar. 7, 2023

(54) INSTRUMENTED FRACTURING TARGET FOR DATA CAPTURE OF SIMULATED WELL

(71) Applicant: Halliburton Energy Services, Inc., Houston, TX (US)

(72) Inventors: James Marshall Barker, Mansfield, TX (US); Daniel Joshua Stark, Houston, TX (US); Hazim Hussein Abass, Pearland, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 574 days.

(21) Appl. No.: 16/500,372

(22) PCT Filed: Dec. 28, 2018

(86) PCT No.: PCT/US2018/067990
§ 371 (c)(1),
(2) Date: Oct. 2, 2019

(87) PCT Pub. No.: WO2020/139386
PCT Pub. Date: Jul. 2, 2020

(65) Prior Publication Data
US 2021/0181372 A1 Jun. 17, 2021

(51) Int. Cl.
*G01V 99/00* (2009.01)
*E21B 43/116* (2006.01)
(Continued)

(52) U.S. Cl.
CPC .......... *G01V 99/005* (2013.01); *E21B 43/116* (2013.01); *E21B 43/26* (2013.01); *G01N 33/24* (2013.01)

(58) Field of Classification Search
CPC ...... E21B 43/116; E21B 47/12; E21B 43/119; E21B 43/26; E21B 43/11; E21B 43/117;
(Continued)

(56) References Cited

U.S. PATENT DOCUMENTS

| 5,106,164 A | 4/1992 | Kitzinger et al. |
| 8,899,320 B2 | 12/2014 | Le |

(Continued)

FOREIGN PATENT DOCUMENTS

| CN | 201908649 U | * | 7/2011 |
| CN | 107269263 A | * | 10/2017 |

OTHER PUBLICATIONS

PCT Application Serial No. PCT/US2018/067990, International Search Report, dated Sep. 25, 2019, 4 pages.
(Continued)

*Primary Examiner* — Zakiya W Bates
(74) *Attorney, Agent, or Firm* — DeLizio, Peacock, Lewin & Guerra

(57) ABSTRACT

Construction and use of an instrument test fixture for capturing performance data for stimulation or fracturing treatments. The test fixture includes a target material, such as concrete, which includes embedded sensors surrounding a casing. An energetic stimulation treatment, such as a dynamic pulse fracturing technique, is applied through the casing to the target material to simulate a treatment that would be performed in a wellbore. During application of the treatment, the sensors capture measurements which are recorded for analysis by a data collection system. The sensors allow for the measurement of key performance indicators including static and dynamic pressure, generated temperature, and resulting strain energy. The captured data can be analyzed and used to design and optimize stimulation treatments for field applications.

20 Claims, 4 Drawing Sheets

(51) Int. Cl.
  *E21B 43/26* (2006.01)
  *G01N 33/24* (2006.01)
(58) Field of Classification Search
  CPC ........ E21B 43/12; E21B 49/00; E21B 43/263;
         E21B 47/06; E21B 47/00; G01N 33/24
  See application file for complete search history.

(56) References Cited

U.S. PATENT DOCUMENTS

| | | | |
|---|---|---|---|
| 9,738,824 | B2 | 8/2017 | Al-Nakhli et al. |
| 9,791,108 | B2 | 10/2017 | Krumrine, III et al. |
| 2003/0150263 | A1 | 8/2003 | Economides et al. |
| 2012/0111560 | A1 | 5/2012 | Hill et al. |
| 2013/0002268 | A1 | 1/2013 | Kumar et al. |
| 2017/0067222 | A1 | 3/2017 | Bell et al. |
| 2017/0205388 | A1* | 7/2017 | Thomas .................. E21B 33/14 |
| 2018/0202277 | A1 | 7/2018 | Sawka et al. |
| 2021/0040813 | A1* | 2/2021 | Inyang .................... E21B 33/13 |

OTHER PUBLICATIONS

PCT Application Serial No. PCT/US2018/067990, International Written Opinion, dated Sep. 25, 2019, 6 pages.

Bayless, "Oil Well Stimulation with Hydrogen Peroxide", 1997, Society of Petroleum Engineers.

Gaydecki, et al., "Propagation and Attenuation of Medium-Frequency Ultrasonic Waves in Concrete: A Signal Analytical Approach", Measurement Science and Technology, vol. 3, No. 1, 1992, pp. 126-134.

Warpinski, et al., "Autonomous Microexplosives Subsurface Tracing System Final Report", Sandia National Laboratories, Apr. 1, 2004, 70 pages.

* cited by examiner ced sensors surrounding a casing. An energetic stimulation treatment, such as a dynamic pulse fracturing technique, is applied through the casing to the target material to simulate a treatment that would be performed in a wellbore. During application of the treatment, the sensors capture measurements which are recorded for analysis by a data collection system. The sensors allow for the measurement of key performance indicators including static and dynamic pressure, generated temperature, and resulting strain energy. The captured data can be analyzed and used to design and optimize stimulation treatments for field applications.

INSTRUMENTED FRACTURING TARGET FOR DATA CAPTURE OF SIMULATED WELL

TECHNICAL FIELD

The disclosure generally relates to the field of earth or rock drilling (mining), and more particularly to testing and analysis of downhole stimulation treatments, such as fracturing.

BACKGROUND ART

Fracturing is utilized to stimulate the production of hydrocarbons from subterranean formations penetrated by well bores. For example, when performing hydraulic fracturing treatments, a portion of a formation to be fractured is isolated using conventional packers or the like, and a fracturing fluid is pumped through the wellbore into the isolated portion of the formation to be stimulated at a rate and pressure such that fractures are formed and extended in the formation. The fractures provide conductive channels in the formation through which produced fluids can readily flow to the well bore. To facilitate the fracturing operation, a casing placed in the wellbore can be perforated using an explosive charge. The perforation and fracturing techniques utilized can vary depending upon features and properties of the formation.

BRIEF DESCRIPTION OF THE DRAWINGS

Embodiments of the disclosure may be better understood by referencing the accompanying drawings.

DESCRIPTION OF EMBODIMENTS

The description that follows includes example systems, methods, techniques, and program flows that embody embodiments of the disclosure. However, it is understood that this disclosure may be practiced without these specific details. For instance, this disclosure refers to dynamic pulse fracturing in illustrative examples. Embodiments of this disclosure can be also applied to experimenting with other fracturing techniques including hydraulic, explosive, and gas gun techniques. In other instances, well-known instruction instances, protocols, structures and techniques have not been shown in detail in order not to obfuscate the description.

Overview

Figure 1:
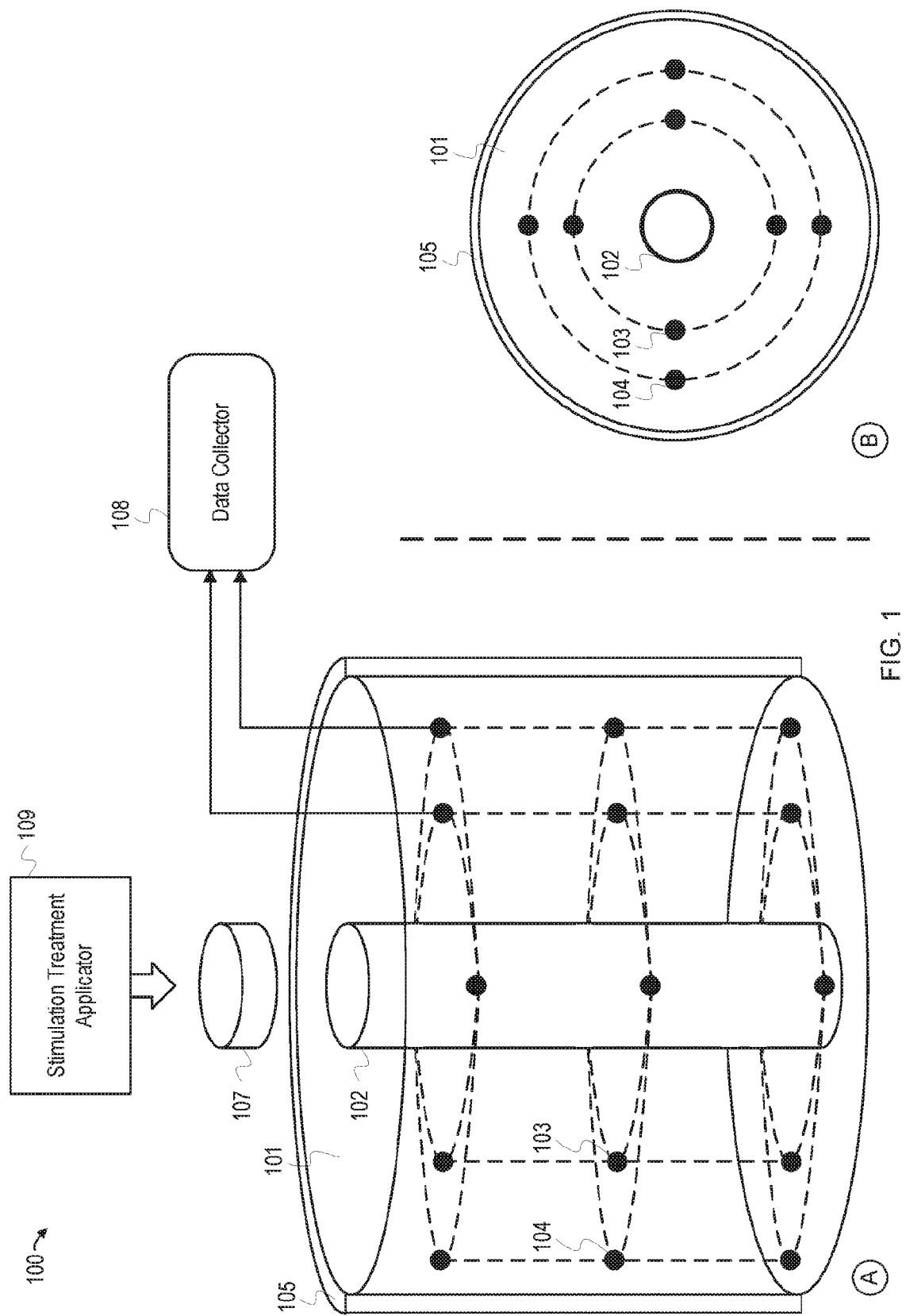
FIG. 1 depicts a schematic diagram of a test fixture for use in simulating and capturing data for downhole stimulation treatments.

This disclosure describes the construction and use of an instrument test fixture for capturing performance data for stimulation or fracturing treatments. The test fixture includes a target material, such as concrete, which includes embed- Example Illustrations FIG. 1 depicts a schematic diagram of a test fixture for use in simulating and capturing data for downhole stimulation treatments. FIG. 1 depicts an instrumented test fixture 100 which includes a target material 101, a casing 102, a first fiber optic loop 103, a second fiber optic loop 104, an outer form 105, and a cap 107. The first fiber optic loop 103 and the second fiber optic loop 104 are communicatively coupled to a data collector ("collector 108"). A stimulation treatment applicator 109 operates on the test fixture 100 to apply stimulation treatments, such as dynamic pulse fracturing treatments including gas-generating propellants, exothermic chemical reactions, and pulse-power plasma discharge. FIG. 1 includes a plan view of the test fixture 100 marked with the letter A, and a top cross-sectional view of the test fixture 100 marked with the letter B.

The target material 101 may be concrete that is poured into the outer form 105 (which has been cut away in FIG. 1 for purposes of illustration). The target material 101, however, is not limited to concrete and can include other materials such as cement, core samples extracted from a formation, metal, plastic, composite material, rock, epoxy-cured resins, or any combination of the foregoing. The target material 101 can be tailored to represent downhole formations. For example, a density or shape of the target material 101 or a portion of the target material 101 may be modeled after a downhole formation. The target material 101 may be designed to meet specified environmental properties such as mechanical strength, density, mineralogy, rheology, and potential of Hydrogen (pH) level. These properties and other attributes of the target material 101, such as additives, curing time, volume, etc., can be recorded by the collector 108. The outer form 105, and the target material 101 as a result, may vary in shape and size. The outer form 105 may be, for example, a cylindrical shell such as a 55-gallon drum. Additionally, the outer form 105 may be a cube, a sphere, or other shape, and may hold a volume of the target material 101 of 50 cubic feet, 100 cubic meters, etc.

The casing 102 is a metal pipe or tubular core placed at the center of the target material 101. The casing 102 may be a partial piece of casing as would be utilized downhole in a borehole. The casing 102 can be placed in the outer form 105 prior to pouring of the target material 101, or the target material 101 may be drilled after pouring to allow for insertion of the casing 102. The casing 102 may be perforated prior to insertion in the target material 101 or may be perforated after insertion using a charge or string of charges. The charges or string of charges can be of any design used for well stimulation and general casing perforation. Examples include deep penetrating charges, big hole charges, and charges tailored for hydraulic fracturing operations, such as those whose purpose is to generate consistent-sized holes around the circumference of the casing.

The cap 107 is designed to seal an open portion of the casing 102 (such as an end of the pipe) during stimulation treatments. Although only a single cap is depicted, the test fixture 100 can include two caps, one for each end of the casing 102. In some implementations, the bottom portion of the casing 102 may be sealed by the target material 101 itself or be sealed prior to insertion in the target material 101. The cap 107 can be a threaded cap, a plug, or other means to contain the pressure generated during perforation and dynamic-pulse-fracturing events. The dynamic pressures and temperature of interests can be up to 100,000 psi and several thousand degrees Fahrenheit depending on the dynamic-pulse-fracturing technique under test. The cap 107 may include one or more holes or fittings (not depicted) which allow for insertion into the casing 102 of equipment, chemicals, or other materials to facilitate a stimulation treatment by the stimulation treatment applicator 109.

The first fiber optic loop 103 and the second fiber optic loop 104 include one or more sensors (represented by the black dots in FIG. 1) which capture data during stimulation treatments. The sensors are arranged in three layers along the longitudinal axis of the target material 101 with four sensors in each layer for each of the loops 103 and 104. As shown in the top cross-sectional view B, the sensors in each layer of the loops 103 and 104 are positioned in concentric circles around the casing 102, the first fiber optic loop 103 having a smaller diameter than the second fiber optic loop 104. The number and positioning of the sensors in each fiber optic loop and the number of fiber optic loops can vary. For example, each layer may include more or less than 4 sensors, another concentric circle of sensors may be placed outside of the second fiber optic loop 104 or inside of the first fiber optic loop 103, etc. Also, each sensor can be connected to a single fiber cable which connects directly to the collector 108. Additionally, the shape in which the sensors are arranged can vary. The fiber optic loops 103 and 104 need not be concentric. For example, the sensors may be arranged in a circle (as shown in FIG. 1), an ellipse, a rectangle, a square, a cube, a crisscrossing pattern, a spiraling pattern, a zig-zagging pattern, or other geometric pattern. The placement of the sensors may also be random. The sensors can be placed next to, on, or inside the casing 102 or the cap 107, The sensors in the fiber optic loops 103 and 104 can be fixed to a frame or other supporting structure prior to pouring of the target material 101. Alternatively, each layer of the loops 103 and 104 may be placed as the target material 101 is progressively poured into the outer form 105.

Each sensor can be equipped with instrumentation to measure temperature, dynamic or static pressure, and strain. Additionally, sensors may be utilized for measuring acceleration forces, acoustic spectra, dynamic and static strain, static pressure, pH, electromagnetic signals, resistivity, vibration, speed of jet propagation, moment magnitudes, etc. Although referred to as sensors in a fiber optic loop, the sensors may be a combination of fiber optic, electrical, or mechanical sensors and may be connected using fiber optic cable, copper wiring, etc. The sensors can be point sensors, such as geophones; accelerometers; strain gauges; pressure gauges; electromagnetic sensors; MEMS sensors; voltmeters; ammeters; charge sensors; electrometers; coulomb meter; and electrochemical potentiometers, such as a pH meter. The sensors can also be distributed sensors, such as a distributed acoustic sensing optical fiber system; distributed temperature sensing optical fiber system; distributed strain sensing optical fiber system; Sagnac interferometry; and Michelson interferometry. The sensors can also be quasi-distributed sensors, in which a series of point sensors are connected and utilize the same communication line, such as fiber Bragg gratings in an optical fiber system. When installing sensors, such as point sensors, the target material 101 may be drilled after curing or partially curing to allow for the insertion of the sensors at various locations throughout the target material 101. Multiple sensors and sensors of different types, such as those described above, can be used or implemented in the same form, using fiber optic lines and accelerometers for example. Also, at least for fiber optic lines, the same fiber can handle multiple sensing systems simultaneously. For example, DTS (distributed temperature sensing), DAS (distributed acoustic sensing), and fiber Bragg gratings could all be on the same fiber and can be processed separately (e.g., using wavelength-division multiplexing or time-domain multiplexing).

During application of a stimulation treatment or perforation, the collector 108 receives and stores measured data captured by the sensors of the first fiber optic loop 103 and the second fiber optic loop 104. The collector 108 may initiate a stimulation treatment by communicating with the stimulation treatment applicator 109. For example, the collector 108 transmits a message to a controller of the stimulation treatment applicator 109 instructing the controller to release chemicals into the casing 102. The collector 108 can store the data captured from the sensors of the first fiber optic loop 103 and the second fiber optic loop 104 throughout application of the stimulation treatment as time series data in a database. The sensors may be equipped with distinct telemetry identifiers, such as a unique tag, header, or a TCP/IP address which can be used by the collector 108 to identify and communicate with each sensor. The collector 108 associates the measurements from each sensor with their corresponding identifier. The collector 108 can analyze the data and provide key performance metrics such as highest pressure generated during the treatment, highest temperature, highest dynamic strain, highest static strain, etc. The collector 108 can also perform machine learning and statistical analysis on the data to generate and train models for optimizing future stimulation treatments. Additional stimulation treatments can be sequentially applied multiple times in the same test fixture 100 such that fracture propagation and extension can be measured during each application of the treatments.

In some instances, an experimentation process for stimulation treatments may involve multiple test fixtures 100. To ensure uniformity in placement of sensors in the fiber optic loops 103 and 104 across the multiple test fixtures 100, a mold or form may be used during placement of the sensors into the target material 101. Alternatively, dimensions for the location of each sensor may be measured and used during placement of sensors for each of the test fixtures 100.

In addition to the casing 102 and the loops 103 and 104, other components may be embedded into the target material 101 to facilitate stimulation treatments. For example, heat pipes can be embedded in the target material 101 for use in raising the temperature of the casing 102 and the target material 101. The heat pipes may be controlled by the collector 108 or the stimulation treatment applicator 109.

Figure 2:
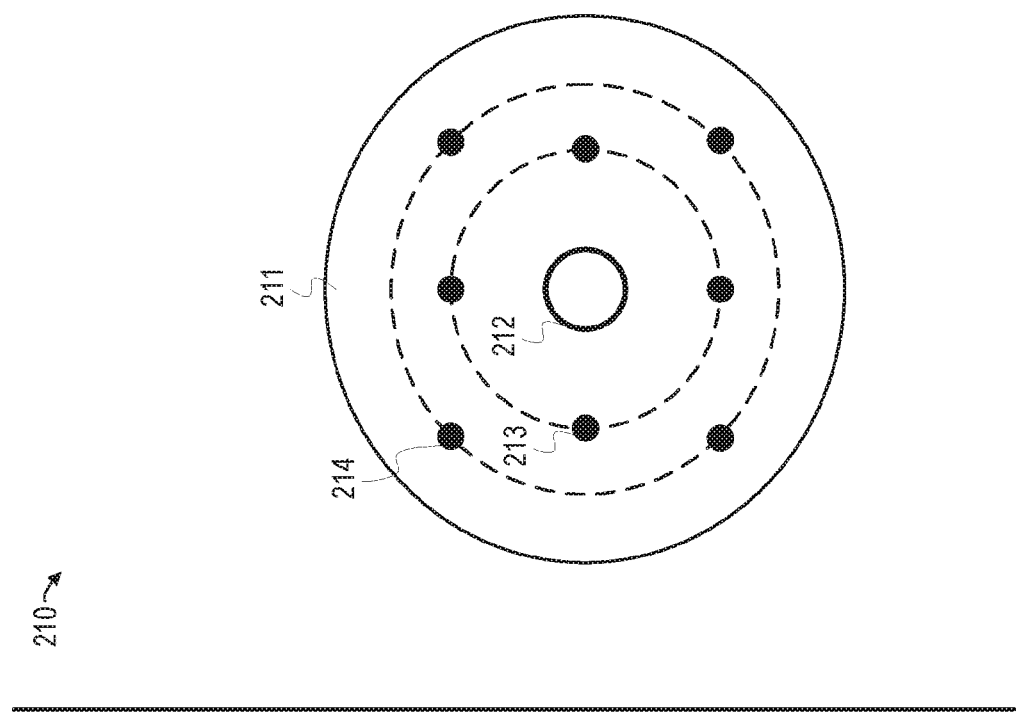
FIG. 2 depicts schematic diagrams of example embodiments of test fixtures for use in simulating and capturing data for downhole stimulation treatments.
Figure 2:
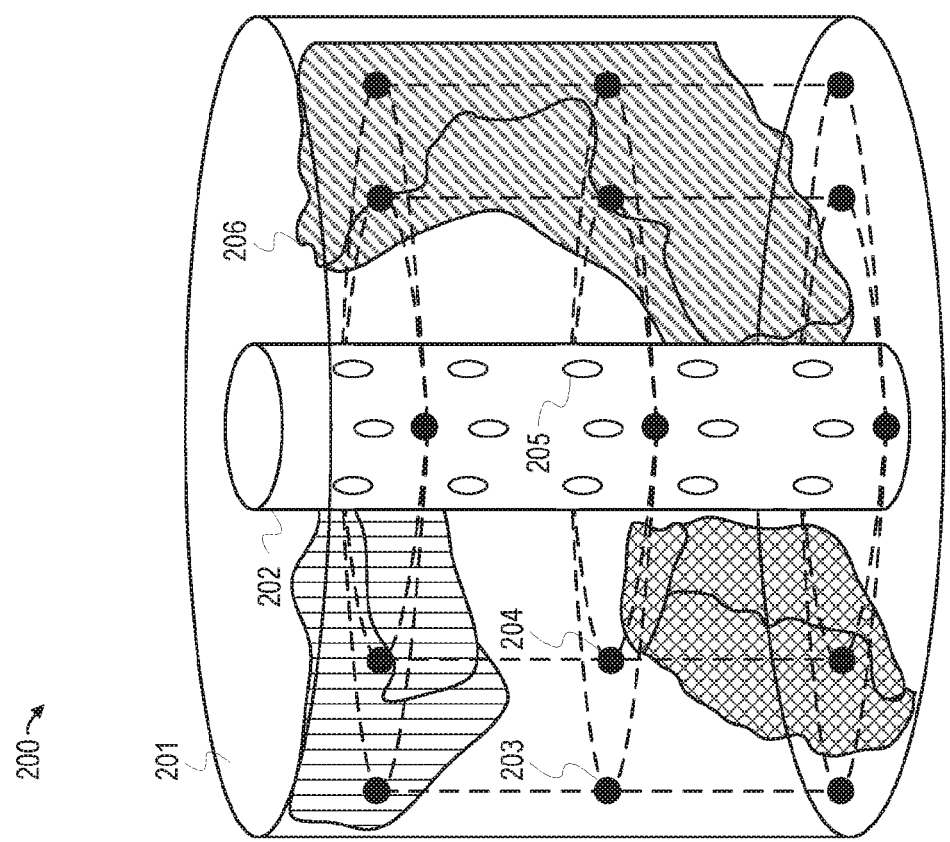

FIG. 2 depicts schematic diagrams of example embodiments of test fixtures for use in simulating and capturing data for downhole stimulation treatments. FIG. 2 depicts a first embodiment of a test fixture 200 and a top cross-sectional view of a second embodiment a test fixture 210.

Similar to the test fixture 100, the test fixture 200 includes target material 201, a casing 202, a first fiber optic loop 203, and a second fiber optic loop 204. The test fixture 200 also includes formation samples 206 which have been embedded in the target material 201. The formation samples 206 may be rock or core samples from a formation for which a perforation or stimulation treatment is being designed. The formation samples 206 can be extracted after application of a treatment and analyzed to determine mechanical properties of the formation samples 206 and the effect of the treatment. The determined mechanical properties of the formation samples 206 can be used to model stimulation treatments for the formation from which the formation samples 206 were extracted. The formation samples 206 may include one or more core samples that can be embedded within the target material 201 and positioned to surround the casing 202. Similar to the mechanical properties, other measurements such as pressure, temperature, and strain can be obtained from sensors next to or within the core samples and be used to improve models or simulations of treatments for a downhole formation.

The test fixture 200 also includes perforations 205 in the casing 202. The perforations 205 may have been created prior to installation of the casing 202 in the target material 201. The casing 202 can be installed so that one or more of the perforations 205 are directed toward sensors in the fiber optic loops 203 and 204. Conversely, the loops 203 and 204 may be installed so that sensors are in line with one or more of the perforations 205. The size, shape, and quantity of the perforations 205 can vary.

The test fixture 210 includes target material 211, a casing 212, a first fiber optic loop 213, and a second fiber optic loop 214. As illustrated by the black dots representing sensors in the loops 213 and 214, the sensors in the second fiber optic loop 214 have been staggered from the sensors of the first fiber optic loop 213. For some sensor types, such as accelerometers, the measurement obtained by the sensor may be affected by an obstacle, such as another sensor or cable, in between the sensor and the casing 212. Loops or sensors in addition to those pictured in FIG. 2 can be similarly staggered so that sensors have a clear line of sight to the casing 202, with the exception of intervening target material 201. Additionally, the arrangement of cables for connecting sensors in the target material 211 can be optimized to avoid interfering with sensor measurements. For example, a cable for a single sensor, as opposed to multiple sensors in a loop, may be run in a radial fashion from the sensor to the outer perimeter of the target material 211. As an additional example, fiber optic cable and the sensors in a loop, such as the first fiber optic loop 213, may be arranged in a spiral extending along the longitudinal axis of the test fixture 210. Other arrangements of sensors are possible, such as hatchpatterns, crisscrosses, basket weaves, zig-zags, or combinations of curved and linear (in x, y, z, radial, or a diagonal direction). Also, the arrangement of sensors can vary based on types of the sensors. For example, in the same test fixture, fiber optic sensors may be placed in a circular pattern, accelerometers in another pattern (e.g., a sphere, a hexagonal closed pack design, a firework or starburst shaped pattern), and geophones in yet another pattern.

Figure 3:
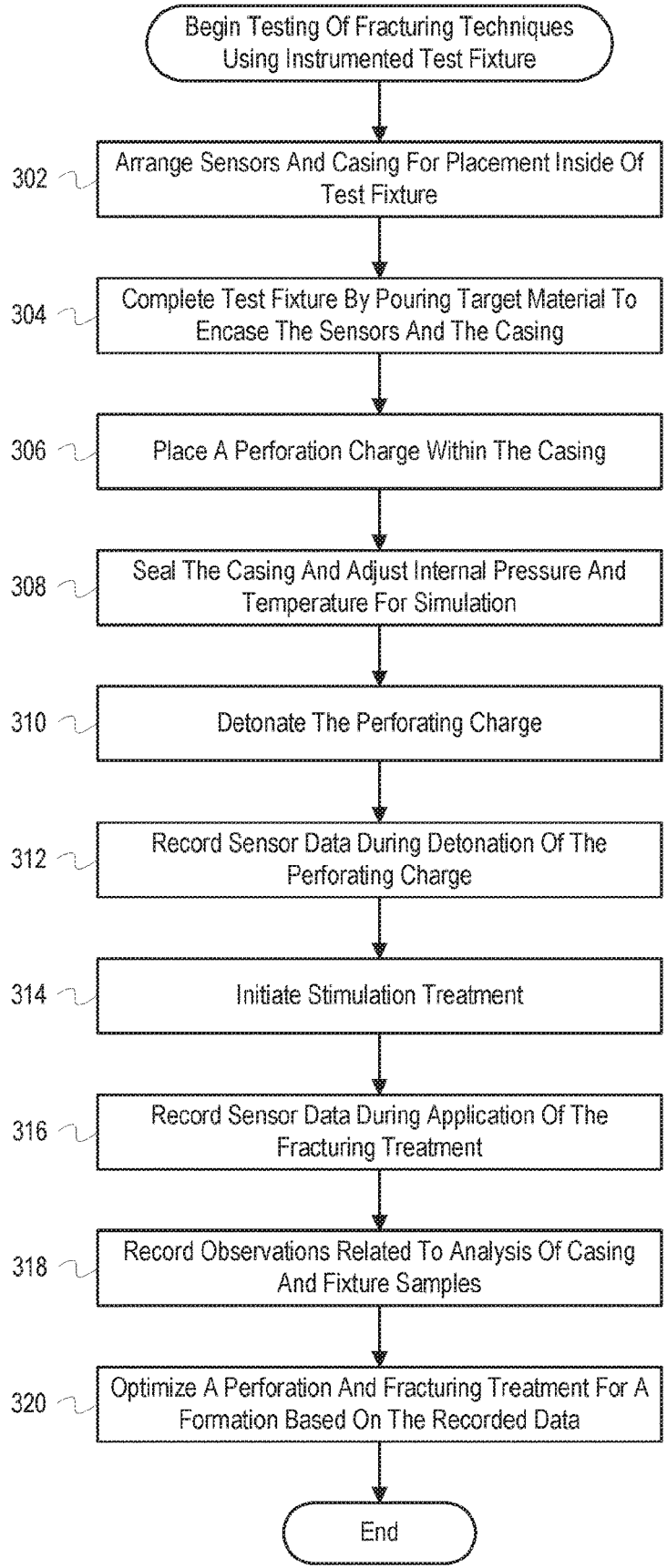
FIG. 3 depicts example operations for testing of fracturing techniques using an instrumented test fixture.

FIG. 3 depicts example operations for testing of fracturing techniques using an instrumented test fixture. FIG. 3 refers to a data collector as performing some operations. The term "data collector" is used for naming consistency with FIG. 1, although naming of program code can vary among implementations. Some operations of FIG. 3 may be performed by an operator, such as a test engineer, who physically manipulates or controls components of the test fixture or stimulation treatments. Such actions can be automated using a combination of machinery, hardware, and software, such as the data collector.

Sensors and a casing are arranged for placement inside of a test fixture (302). The sensors can be attached to a wire frame, placed in a mold, or otherwise fixed in space by a support structure. Some sensors may be coated with protective material or placed inside housings to protect the sensors from a target material, perforations, or treatments to be applied. Additionally, the sensors are configured for communication with a data collector ("collector"). The sensors may be connected or plugged into each other in a loop which is fed back to the collector or be individually connected, either physically or wirelessly, to the collector. The location and orientation of each sensor may be measured relative to a point within the test fixture (e.g., a center of the casing, another sensor, a determined plane) and the location and orientation stored by the data collector. For example, the radial distance between each sensor and the casing may be recorded as well as an angle or orientation of the sensor relative to the casing or a determined plane. Additionally, the distance between an inner sensor and an outer sensor may be measured and stored. Furthermore, other parameters of the sensors, such as drift, sensitivity, and bias voltages, can also be recorded and can be used to improve optimization of the sensors across experiments. For example, the sensitivity of a sensor can be increased to improve measurements detected by a sensor. The casing may be fixed/attached to an outer form or otherwise arranged to be within a center of the test fixture. In some implementations, the casing may be placed in a location other than the center of the test fixture. For example, if testing a unidirectional perforating charge, the casing may be placed near the outer perimeter of the test fixture so that more target material will be available to receive a detonation of the perforating charge.

The test fixture is completed by pouring target material to encase the sensors and the casing (304). The target material may be concrete, cement, plastic, metal, composite material, or resin which is poured into an outer form for the test fixture to envelop the sensors and at least a portion of the casing. Some of the casing may protrude from the target material. Core or rock samples can be placed as the target material is being poured. Similarly, the sensors or casing may be placed or adjusted as the target material is being poured.

A perforation charge is placed within the casing (306). In instances where the casing is not perforated prior to placement in the test fixture, a perforating charge can be used to perforate the casing and prepare the casing and the target material for receiving a stimulation treatment.

The casing is sealed and an internal pressure and temperature is adjusted for simulation of a downhole environment (308). A cap may be screwed on or otherwise attached to one or both ends of the casing as needed in order to create a sealed environment. The internal pressure and temperature of the casing can be raised or lowered to simulate conditions of a downhole environment in which stimulation treatments may be applied. Additionally, the temperature of the target material may be raised or lowered to simulate downhole conditions, in some implementations, the entire test fixture may be sealed so that the pressure of the target material can also be increased.

The perforating charge is detonated (310). If a perforating charge was placed inside the casing, the perforating charge can be detonated to create perforations in the casing. The collector may trigger the perforating charge and can record data captured by the sensors during the detonation.

The collector records sensor data during detonation of the perforating charge (312). During detonation of the perforating charge, the collector receives measurements from the sensors and records the data in a database or other storage device. The measurements for each sensor are recorded and tagged with an identifier for the sensor. The measurements can include acoustics, temperature, electric charge, pH, pressure, etc. Using the locations and orientation of the sensors in conjunction with the recorded data, the collector can determine dimensions of the perforation volume, energy transfer efficiency, charge directionality and penetration depth, and other similar measurements without having to break open or inspect the test fixture. In some implementations, additional sensors may be added to the test fixture after perforation and before initiation of a stimulation treatment. For example, if a sensor may be damaged by the perforation charge, the sensor may be added to the test fixture after detonating the perforating charge by drilling a hole in the side of the test material for inserting the sensor.

A stimulation treatment is initiated (314). Materials necessary to generate stimulation treatment, such as gas-generating propellants, chemicals for exothermic chemical reactions, and plasma, are inserted into the casing. In some instances, multiple stimulation treatments are sequentially applied. The amount and type of materials applied for the stimulation treatment(s) can be recorded by the collector and associated with an experiment identifier.

The collector records sensor data during application of the stimulation treatment (316). While the stimulation treatment is being applied, the collector receives measurements from the sensors and records the data in a database or other storage device. The measurements for each sensor are recorded and tagged with an identifier for the sensor. The identifier for each sensor can be associated with attributes of the sensor such as its location and orientation within the test fixture. The collector can use the location to determine additional metrics such as a propagation speed of the treatment. Propagation speed can be determined based on a time at which each sensor detected the arrival of a treatment, e.g., detected increased temperature or strain, and the relative location of at least two sensors. The recorded data and determined metrics can be associated with the experiment identifier used for tracking attributes and data of each experiment, such as a type of treatment applied, a target material used, a perforating charge used, etc. Using the experiment identifier, the collector can analyze recorded measurements across the different experiments. Based on this analysis, the collector can determine relative properties of the experiments such as the effect on pressure within the target material caused by different chemical combinations.

The collector records observations related to analysis of casing and target material samples (318). The test fixture may be cut or broken open to extract the casing and portions of the target material for analysis. The analysis of extracted casing, concrete, or any embedded fixture samples can identify geometry of perforation volume, geometry of blasting hole in casing, penetration depth of perforation or fractures, fracture propagation and extent, and mineralogy of transformed perforation volume. The analysis can be conducted utilizing techniques such as computed X-Ray tomography (CT) scan, nuclear magnetic resonance, electromagnetic and acoustic scanning, and optical evaluation with the volume extracted through standard image processing techniques. Any observations or data collected as a result of this analysis can be recorded by the collector and tagged with the experiment identifier. The collector can correlate this data with the sensor data to determine additional observations, such as a relationship between temperature and fracture propagation.

The collector optimizes a perforation and stimulation treatment for a formation based on the recorded data (320). The collector can perform analysis, such as machine learning or methods utilized from Design of Experiments, on the experiment data to generate a calibrated model for designing and optimizing treatments for a formation in which the treatment will be applied. The model may take as inputs the type of rock and other features of the formation; a desired temperature, pressure, or strain to be created by the treatment; a time for the treatment; etc. The collector can also calibrate dynamic stimulation treatment models and dynamic shock models. Furthermore, after a number of experiments, the collector can determine and characterize a fracturing response (e.g., temperature, time, and pressure) for various stimulation treatments. Using the determined responses, the collector can suggest or determine ideal treatments for given scenarios. For example, based on provided formation properties (e.g., rock type, rock mechanics, etc.), the collector can identify stimulation treatments which may be suitable based on the treatments being able to sustain a pressure above a minimum threshold for a prolonged period. As an additional example, if the formation has particularly dense or hard rock, the collector may identify a stimulation treatment that has a high maximum temperature and pressure.

Variations

The flowcharts are provided to aid in understanding the illustrations and are not to be used to limit scope of the claims. The flowcharts depict example operations that can vary within the scope of the claims. Additional operations may be performed; fewer operations may be performed; the operations may be performed in parallel; and the operations may be performed in a different order. For example, the operations depicted in blocks 302 and 304 can be performed in parallel or concurrently. Additionally, a perforating charge, and therefore blocks 306 and 310, may not be necessary. It will be understood that each block of the flowchart illustrations and/or block diagrams, and combinations of blocks in the flowchart illustrations and/or block diagrams, can be implemented by program code. The program code may be provided to a processor of a general purpose computer, special purpose computer, or other programmable machine or apparatus.

As will be appreciated, aspects of the disclosure may be embodied as a system, method or program code/instructions stored in one or more machine-readable media. Accordingly, aspects may take the form of hardware, software (including firmware, resident software, micro-code, etc.), or a combination of software and hardware aspects that may all generally be referred to herein as a "circuit," "module" or "system." The functionality presented as individual modules/units in the example illustrations can be organized differently in accordance with any one of platform (operating system and/or hardware), application ecosystem, interfaces, programmer preferences, programming language, administrator preferences, etc.

Any combination of one or more machine readable medium(s) may be utilized. The machine readable medium may be a machine readable signal medium or a machine readable storage medium. A machine readable storage medium may be, for example, but not limited to, a system, apparatus, or device, that employs any one of or combination of electronic, magnetic, optical, electromagnetic, infrared, or semiconductor technology to store program code. More specific examples (a non-exhaustive list) of the machine readable storage medium would include the following: a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a machine readable storage medium may be any tangible medium that can contain, or store a program for use by or in connection with an instruction execution system, apparatus, or device. A machine readable storage medium is not a machine readable signal medium.

A machine readable signal medium may include a propagated data signal with machine readable program code embodied therein, for example, in baseband or as part of a carrier wave. Such a propagated signal may take any of a variety of forms, including, but not limited to, electromagnetic, optical, or any suitable combination thereof. A machine readable signal medium may be any machine readable medium that is not a machine readable storage medium and that can communicate, propagate, or transport a program for use by or in connection with an instruction execution system, apparatus, or device.

Program code embodied on a machine readable medium may be transmitted using any appropriate medium, including but not limited to wireless, wireline, optical fiber cable, RF, terahertz, etc., or any suitable combination of the foregoing.

Computer program code for carrying out operations for aspects of the disclosure may be written in any combination of one or more programming languages, including an object oriented programming language such as the Java® programming language, C++ or the like; a dynamic programming language such as Python; a scripting language such as Perl programming language or PowerShell script language; and conventional procedural programming languages, such as the "C" programming language or similar programming languages. The program code may execute entirely on a stand-alone machine, may execute in a distributed manner across multiple machines, and may execute on one machine while providing results and or accepting input on another machine.

The program code/instructions may also be stored in a machine readable medium that can direct a machine to function in a particular manner, such that the instructions stored in the machine readable medium produce an article of manufacture including instructions which implement the function/act specified in the flowchart and/or block diagram block or blocks.

Figure 4:
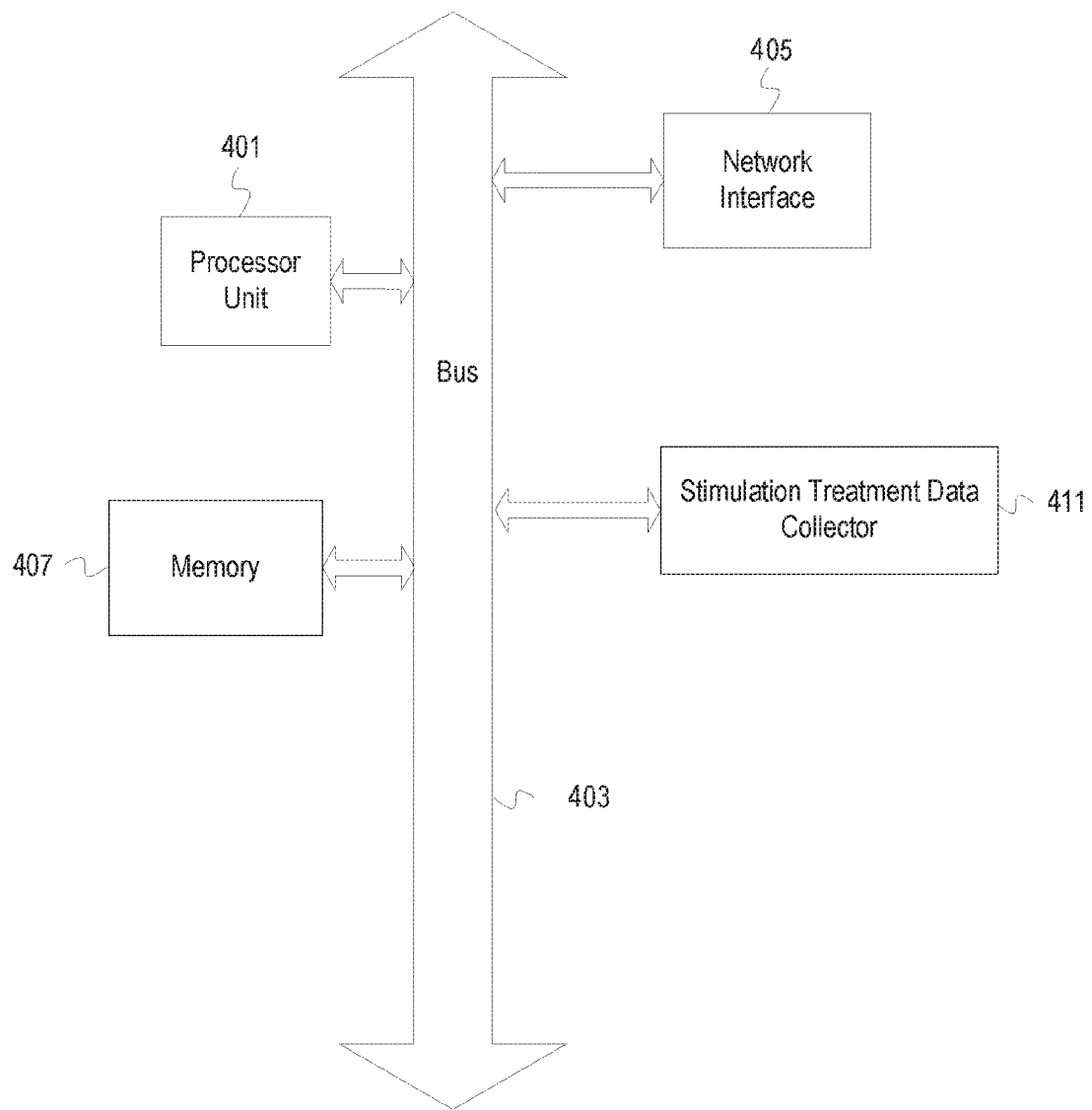
FIG. 4 depicts an example computer system with a stimulation treatment data collector.

FIG. 4 depicts an example computer system with a stimulation treatment data collector. The computer system includes a processor unit 401 (possibly including multiple processors, multiple cores, multiple nodes, and/or implementing multi-threading, etc.). The computer system includes memory 407. The memory 407 may be system memory (e.g., one or more of cache, SRAM, DRAM, zero capacitor RAM, Twin Transistor RAM, eDRAM, EDO RAM, DDR RAM, EEPROM, NRAM, RRAM, SONOS, PRAM, etc.) or any one or more of the above already described possible realizations of machine-readable media. The computer system also includes a bus 403 (e.g., PCI, ISA, PCI-Express, HyperTransport® bus, InfiniBand® bus, NuBus, etc.) and a network interface 405 (e.g., a Fiber Channel interface, an Ethernet interface, an internet small computer system interface, SONET interface, wireless interface, etc.). The system also includes stimulation treatment data collector 411. The stimulation treatment data collector 411 can control fracturing stimulation treatments for a test fixture and record data from sensors embedded in the test fixture. The stimulation treatment data collector 411 can also analyze the data to customize perforation and stimulation treatments for a proposed formation, Any one of the previously described functionalities may be partially (or entirely) implemented in hardware and or on the processor unit 401. For example, the functionality may be implemented with an application specific integrated circuit, in logic implemented in the processor unit 401, in a co-processor on a peripheral device or card, etc. Further, realizations may include fewer or additional components not illustrated in FIG. 4 (e.g., video cards, audio cards, additional network interfaces, peripheral devices, etc.). The processor unit 401 and the network interface 405 are coupled to the bus 403. Although illustrated as being coupled to the bus 403, the memory 407 may be coupled to the processor unit 401.

While the aspects of the disclosure are described with reference to various implementations and exploitations, it will be understood that these aspects are illustrative and that the scope of the claims is not limited to them. In general, techniques for constructing and utilizing a stimulation treatment test fixture as described herein may be implemented with facilities consistent with any hardware system or hardware systems, Many variations, modifications, additions, and improvements are possible.

Example Embodiments

A. An apparatus that includes a target material; a casing located within the target material; and a first set of sensors embedded within the target material.

B. An apparatus that includes a concrete fixture; a casing located within the concrete fixture; a set of sensors embedded within the concrete fixture; a processor; and a machine-readable medium having program code executable by the processor to cause the apparatus to, during application of a stimulation treatment, capture first measurements from the set of sensors.

C. A method that includes constructing a test fixture comprising a target material, a casing positioned within the target material, and a set of sensors; applying a stimulation treatment to the test fixture; and during application of the stimulation treatment, capturing data from the set of sensors.

Each of the embodiments A. B, and C may have one or more of the following additional elements in any combination.

Element 1: wherein the casing is perforated prior to insertion in the target material.

Element 2: further comprising a perforating charge positioned within the casing, wherein the perforating charge is detonated to perforate the casing after insertion of the casing in the target material.

Element 3: further comprising a cap for sealing an open portion of the casing.

Element 4: wherein the first set of sensors form at least one of a circle, a sphere, a spiral, a square, a diamond, a cross-hatch pattern, a rectangle, and an ellipse around the casing.

Element 5: further comprising a second set of sensors, wherein the second set of sensors are positioned farther from the casing than the first set of sensors and are staggered in relation to the first set of sensors relative to the casing.

Element 6: wherein the first set of sensors comprise at least one of a temperature sensor, a pressure gauge, a strain gauge, an accelerometer, and an electromagnetic sensor.

Element 7: further comprising samples embedded within the target material, wherein the samples were extracted from a formation.

Element 8: wherein the target material comprises at least one of concrete, cement, resin, metal, plastic, composite material, rock, and a core sample extracted from a formation.

Element 9: further comprising a perforating charge positioned within the casing, wherein the perforating charge is detonated to perforate the casing; and further comprising program code to capture second measurements from the set of sensors during detonation of the perforating charge.

Element 10: wherein the concrete fixture further comprises at least one of a core sample embedded adjacent to the casing, resin, plastic, metal, composite material, cement, and rock.

Element 11: wherein the program code to capture the first measurements from the set of sensors comprises program code to capture at least one of temperature, strain, pressure, position, velocity, acceleration, acoustic spectrum, time of arrival, or forces.

Element 12: inserting a perforating charge in the casing; detonating the perforating charge; and during detonation of the perforating charge, capturing second data from the set of sensors.

Element 13: wherein constructing the test fixture comprises positioning the set of sensors to form at least one of a circle, a sphere, a spiral, a square, a diamond, a cross-hatch pattern, a rectangle, and an ellipse around the casing; and embedding the casing and the set of sensors in the target material.

Element 14: wherein positioning the set of sensors comprises affixing at least one sensor of the set of sensors to a supporting structure.

Element 15: wherein embedding the casing and the set of sensors in the target material comprises pouring at least one of concrete, cement, metal, plastic, composite material, and resin to envelop the set of sensors and at least a portion of the casing.

Element 16: wherein the test fixture further comprises at least one of core samples and rocks embedded within the target material.

Element 17: wherein applying the stimulation treatment to the test fixture comprises applying a dynamic pulse fracturing treatment comprising at least one of gas-generating propellants, exothermic chemical reactions, and pulse-power plasma discharge.

By way of non-limiting example, exemplary combinations applicable to A, B, and C include Elements 14 and 15 with Element 13.

Plural instances may be provided for components, operations or structures described herein as a single instance. Finally, boundaries between various components, operations and data stores are somewhat arbitrary, and particular operations are illustrated in the context of specific illustrative configurations. Other allocations of functionality are envisioned and may fall within the scope of the disclosure. In general, structures and functionality presented as separate components in the example configurations may be implemented as a combined structure or component. Similarly, structures and functionality presented as a single component may be implemented as separate components. These and other variations, modifications, additions, and improvements may fall within the scope of the disclosure.

Use of the phrase at least one of preceding a list with the conjunction "and" should not be treated as an exclusive list and should not be construed as a list of categories with one item from each category, unless specifically stated otherwise. A clause that recites "at least one of A, B, and C" can be infringed with only one of the listed items, multiple of the listed items, and one or more of the items in the list and another item not listed.

What is claimed is:

1. A test fixture configured to sense conditions in a simulated downhole environment, comprising:
   a target material inside the test fixture;
   a casing located within the target material;
   a first set of sensors embedded within the target material to sense conditions in the simulated downhole environment in the test fixture; and
   a data collector configured to record the conditions from the first set of sensors and calibrate dynamic stimulation treatment models based on the recorded conditions.

2. The test fixture of claim 1, wherein the casing is perforated prior to insertion in the target material.

3. The test fixture of claim 1 further comprising a perforating charge positioned within the casing, wherein the perforating charge is detonated to perforate the casing after insertion of the casing in the target material.

4. The test fixture of claim 1 further comprising a cap for sealing an open portion of the casing.

5. The test fixture of claim 1, wherein the first set of sensors form at least one of a circle, a sphere, a spiral, a square, a diamond, a cross-hatch pattern, a rectangle, and an ellipse around the casing.

6. The test fixture of claim 1 further comprising a second set of sensors, wherein the second set of sensors are positioned farther from the casing than the first set of sensors and are staggered in relation to the first set of sensors relative to the casing.

7. The test fixture of claim 1, wherein the first set of sensors comprise at least one of a temperature sensor, a pressure gauge, a strain gauge, an accelerometer, and an electromagnetic sensor.

8. The test fixture of claim 1 further comprising samples embedded within the target material, wherein the samples were extracted from a formation.

9. The test fixture of claim 1, wherein the target material comprises at least one of concrete, cement, resin, metal, plastic, composite material, rock, and a core sample extracted from a formation.

10. An apparatus comprising:
    a test fixture that simulates a downhole environment, the test fixture including
    a concrete fixture,
    a casing located within the concrete fixture,
    a set of sensors embedded within the concrete fixture,
    a processor; and
    a machine-readable medium having program code executable by the processor to cause the apparatus to, during application of a stimulation treatment, capture first measurements from the set of sensors in the simulated downhole environment and calibrate dynamic stimulation treatment models based on the captured first measurements.

11. The apparatus of claim 10:
    further comprising a perforating charge positioned within the casing, wherein the perforating charge is detonated to perforate the casing; and
    further comprising program code to capture second measurements from the set of sensors during detonation of the perforating charge.

12. The apparatus of claim 10, wherein the concrete fixture further comprises at least one of a core sample embedded adjacent to the casing, resin, plastic, metal, composite material, cement, and rock.

13. The apparatus of claim 10, wherein the program code to capture the first measurements from the set of sensors comprises program code to capture at least one of temperature, strain, pressure, position, velocity, acceleration, acoustic spectrum, time of arrival, or forces.

14. A method comprising:
constructing a test fixture that simulates a downhole environment, the test fixture comprising a target material, a casing positioned within the target material, a set of sensors, and a data collector configured to record conditions from the set of sensors and calibrate dynamic stimulation treatment models based on the recorded conditions;
applying a stimulation treatment to the test fixture; and
during application of the stimulation treatment, capturing data from the set of sensors in the simulated downhole environment.

15. The method of claim 14 further comprising:
inserting a perforating charge in the casing;
detonating the perforating charge; and
during detonation of the perforating charge, capturing second data from the set of sensors.

16. The method of claim 14, wherein constructing the test fixture comprises:
positioning the set of sensors to form at least one of a circle, a sphere, a spiral, a square, a diamond, a cross-hatch pattern, a rectangle, and an ellipse around the casing; and
embedding the casing and the set of sensors in the target material.

17. The method of claim 16, wherein positioning the set of sensors comprises affixing at least one sensor of the set of sensors to a supporting structure.

18. The method of claim 16, wherein embedding the casing and the set of sensors in the target material comprises pouring at least one of concrete, cement, metal, plastic, composite material, and resin to envelop the set of sensors and at least a portion of the casing.

19. The method of claim 14, wherein the test fixture further comprises at least one of core samples and rocks embedded within the target material.

20. The method of claim 14, wherein applying the stimulation treatment to the test fixture comprises applying a dynamic pulse fracturing treatment comprising at least one of gas-generating propellants, exothermic chemical reactions, and pulse-power plasma discharge.

* * * * *